United States Patent
Nakagaki et al.

(10) Patent No.: US 7,153,402 B2
(45) Date of Patent: Dec. 26, 2006

(54) NOX-DECOMPOSING ELECTRODE AND NOX CONCENTRATION-MEASURING APPARATUS

(75) Inventors: Kunihiko Nakagaki, Nagoya (JP); Hideyuki Suzuki, Kasugai (JP); Sang Jae Lee, Ama-Gun (JP); Osamu Nakasone, Inabe-Gun (JP)

(73) Assignee: NGK Insulators, Ltd., Nagoya (JP)

( * ) Notice: Subject to any disclaimer, the term of this patent is extended or adjusted under 35 U.S.C. 154(b) by 667 days.

(21) Appl. No.: 10/419,392

(22) Filed: Apr. 21, 2003

(65) Prior Publication Data

US 2003/0201172 A1  Oct. 30, 2003

(30) Foreign Application Priority Data

Apr. 26, 2002 (JP) ............... 2002-127435

(51) Int. Cl.
*G01N 27/30* (2006.01)
*G01N 27/407* (2006.01)

(52) U.S. Cl. .............. 204/425; 204/290.14; 205/781; 73/23.31

(58) Field of Classification Search .......... 204/290.08, 204/290.14, 424, 426, 429; 205/781, 784, 205/784.5; 73/23.31
See application file for complete search history.

(56) References Cited

U.S. PATENT DOCUMENTS

| | | | |
|---|---|---|---|
| 4,863,583 A * | 9/1989 | Kurachi et al. | 204/424 |
| 6,274,016 B1 | 8/2001 | Hasei et al. | |
| 6,280,588 B1 | 8/2001 | Kato et al. | 789/39 |
| 6,419,818 B1 | 7/2002 | Kato et al. | 789/20 |
| 6,673,223 B1 * | 1/2004 | Kunimoto et al. | 204/426 |

FOREIGN PATENT DOCUMENTS

| | | |
|---|---|---|
| EP | 0 859 233 A2 | 8/1998 |
| EP | 0 971 228 A2 | 1/2000 |
| EP | 1006352 | 6/2000 |
| EP | 1 211 508 A2 | 6/2002 |
| EP | 0 971 228 A3 | 1/2004 |
| JP | 63-266352 | 11/1988 |
| JP | 10-227760 | 8/1998 |
| JP | 11-183434 | 7/1999 |
| JP | 2000-28576 | 1/2000 |
| JP | 2000-171436 | 6/2000 |

OTHER PUBLICATIONS

U.S. Appl. No. 10/419,391, filed Mar. 21, 2003, Nakagaki et al.
Charles T. Lynch, Ph.D., "Practical Handbook of Materials Science", 1989, CRC Press, Tables 6.2-5 and 6.2-6.
Pt-Rh. Density., from "Platinum Metals Review", date unknown.

* cited by examiner

*Primary Examiner*—Kaj K. Olsen
(74) *Attorney, Agent, or Firm*—Burr & Brown

(57) ABSTRACT

A detecting electrode comprises a first cermet electrode layer formed directly on a solid electrolyte layer and a second cermet electrode layer formed on the first cermet electrode layer. The ratio between Pt and Rh in the first cermet electrode layer ranges from 100:0 to 25:75 by weight. The ratio between Pt and Rh in the second cermet electrode layer ranges from 25:75 to 0:100 by weight.

5 Claims, 9 Drawing Sheets

FIG. 3

| NOx CONCENTRATION-MEASURING APPARATUS | Rh (wt%) | Pt (wt%) |
|---|---|---|
| EXAMPLE 1 | 75 | 25 |
| EXAMPLE 2 | 50 | 50 |
| EXAMPLE 3 | 25 | 75 |
| EXAMPLE 4 | 0 | 100 |
| COMPARATIVE EXAMPLE 1 | 90 | 10 |

FIG. 6

| NOx CONCENTRATION-MEASURING APPARATUS | Rh (wt%) | Pt (wt%) |
|---|---|---|
| EXAMPLE 5 | 75 | 25 |
| EXAMPLE 6 | 50 | 50 |
| EXAMPLE 7 | 25 | 75 |
| EXAMPLE 8 | 0 | 100 |
| COMPARATIVE EXAMPLE 2 | 90 | 10 |

NOX-DECOMPOSING ELECTRODE AND NOX CONCENTRATION-MEASURING APPARATUS

BACKGROUND OF THE INVENTION

1. Field of the Invention

The present invention relates to a NOx-decomposing electrode, i.e., an electrode for decomposing or reducing NOx, especially for decomposing NOx to produce oxygen, and to a NOx concentration-measuring apparatus for measuring NOx contained in the atmospheric air or in the exhaust gas discharged from vehicles or automobiles.

2. Description of the Related Art

NOx contained in an exhaust gas discharged from a vehicle or an automobile is measured. In a conventional measuring method, when an exhaust gas discharged from a vehicle or an automobile is introduced as a measurement gas into a sensor which includes a NOx-decomposing electrode, NOx contained in the measurement gas is measured by measuring an electromotive force generated on the NOx-decomposing electrode (see Japanese Laid-Open Patent Publication No. 11-183434). In this method, the NOx-decomposing electrode is a cermet electrode composed of an alloy of Pt—Rh and a ceramic component. The NOx-decomposing electrode is formed on an oxygen ion-conductive solid electrolyte such as zirconia.

The ratio between Pt and Rh (Pt:Rh) in the NOx-decomposing electrode ranges from 10:90 to 99:1 or from 25:75 to 75:25 by weight. When such a ratio is adopted, the oxidation reaction and the reduction reaction of Rh are suppressed on the NOx-decomposing electrode. Further, even if the NOx-decomposing electrode manufactured by the ratio as described above is used for a long period of time, the contact area between the NOx-decomposing electrode and the solid electrolyte is not changed. Accordingly, the impedance of the pumping cell provided in the sensor is not increased. Therefore, a NOx concentration-measuring apparatus using the NOx-decomposing electrode as described above realizes the stabilization of the impedance of the pumping cell and the stabilization of the sensitivity of measurement of NOx.

In such a NOx-decomposing electrode, the ability to decompose NOx is required to be high, and the oxidation reaction and the reduction reaction should be suppressed. The ability to decompose NOx is improved by making the ratio of Rh in the Pt—Rh alloy larger than that of Pt. On the other hand, the oxidation reaction and the reduction reaction are suppressed by making the ratio of Pt in the Pt—Rh alloy larger than that of Rh. Therefore, it is impossible to realize the improvement of the ability to decompose NOx and the suppression of the oxidation reaction and the reduction reaction in the NOx-decomposing electrode as described above.

Further, the NOx-decomposing electrode measures NOx at a high temperature from 700° C. to 800° C. Therefore, the NOx-decomposing electrode repeats the expansion and the contraction every time when NOx is measured. As a result, the NOx-decomposing electrode is exfoliated from the solid electrolyte, and the ability of the NOx concentration-measuring apparatus to measure NOx is lowered.

SUMMARY OF THE INVENTION

The present invention has been made taking the foregoing problems into consideration, and an object thereof is to provide a NOx-decomposing electrode and a NOx concentration-measuring apparatus having high reliability and durability by suppressing the expansion and the contraction of the NOx-decomposing electrode, and by enhancing the ability to decompose NOx by the NOx-decomposing electrode with a multilayered structure of a plurality of cermet electrode layers each including a ceramic component and an alloy in which the ratio between Pt and Rh differs.

According to the present invention, there is provided a NOx-decomposing electrode, i.e., an electrode for decomposing or reducing NOx, especially for decomposing NOx to produce oxygen; wherein the NOx-decomposing electrode has a multilayered structure comprising a plurality of cermet electrode layers each of which includes an alloy of Pt—Rh and a ceramic component; and the respective cermet electrode layers have different ratios between Pt and Rh. The ceramic component is preferably partially stabilized $ZrO_2$ or fully stabilized $ZrO_2$. A stabilizer such as $Y_2O_3$, MgO, CaO, and $CeO_2$ may be used. However, it is especially preferable to use $Y_2O_3$ in view of the sintering at a low temperature.

The NOx-decomposing electrode is formed on a ceramic substrate. Among proportions of Pt in the respective cermet electrode layers, the proportion of Pt in the lowermost cermet electrode layer formed directly on the ceramic substrate is maximum and the proportion of Pt in the uppermost cermet electrode layer is minimum. It is preferable that the material for the ceramic substrate is the same as the material for the NOx-decomposing electrode. It is preferable to use partially stabilized $ZrO_2$ or fully stabilized $ZrO_2$. A stabilizer such as $Y_2O_3$, MgO, CaO, and $CeO_2$ may be used. However, it is especially preferable to use $Y_2O_3$ in view of the sintering at a low temperature.

That is, in the NOx-decomposing electrode, the ratio of Pt is large in the lower cermet electrode layer as compared with the upper cermet electrode layer. Therefore, the oxidation and reduction reactions are suppressed in the cermet electrode layer disposed at the lowermost, and the NOx-decomposing electrode is not exfoliated from the ceramic substrate.

On the other hand, the ratio of Rh is large in the upper cermet electrode layer as compared with the lower cermet electrode layer. Therefore, the ability to decompose NOx is improved in the upper cermet electrode layer.

Therefore, in the NOx-decomposing electrode of the present invention, the oxidation reaction and the reduction reaction are suppressed in the measurement of NOx in the lower cermet electrode layer, and the ability to decompose NOx is improved in the measurement of NOx in the upper cermet electrode layer. Accordingly, the NOx-decomposing electrode has high reliability and a long service life.

In particular, the NOx-decomposing electrode includes a first cermet electrode layer and a second cermet electrode layer which is formed on the first cermet electrode layer; the ratio between Pt and Rh (Pt:Rh) in the first cermet electrode layer ranges from 100:0 to 25:75 by weight; and the ratio between Pt and Rh (Pt:Rh) in the second cermet electrode layer ranges from 25:75 to 0:100 by weight. On this condition, the NOx-decomposing electrode is not exfoliated from the ceramic substrate. As a result, the service life of the NOx-decomposing electrode of the present invention is twice or more as long as the service life of the conventional NOx-decomposing electrode.

In this arrangement, an average particle size of Rh in each of the cermet electrode layers is from 10 to 20 μm. If the average particle size of Rh is less than 10 μm, Rh is moved from a paste having a large ratio of Rh to a paste having a small ratio of Rh when a paste laminate including Pt and Rh is sintered at a high temperature of not less than 1300° C.

Then, a NOx-decomposing electrode, in which the ratio between Pt and Rh is identical in the respective cermet electrode layers, is formed.

In the conventional NOx-decomposing electrode, the exfoliation of the cermet electrode layer from the ceramic substrate is caused at the circumferential edge of the cermet electrode layer. The width of the NOx-decomposing electrode is about several hundreds of µm. On the other hand, the film thickness of the NOx-decomposing electrode is about several tens of µm. Therefore, the width of the NOx-decomposing electrode is extremely larger than the film thickness of the NOx-decomposing electrode.

Accordingly, it is desirable that the adhesive force is further improved between the ceramic substrate and the NOx-decomposing electrode by changing the ratio between Pt and Rh in each of the cermet electrode layers of the NOx-decomposing electrode and changing the ratio between Pt and Rh between the central portion and the circumferential edge of each of the cermet electrode layers of the NOx-decomposing electrode. That is, about the proportions of Pt in the respective cermet electrode layers of the NOx-decomposing electrode formed directly on the ceramic substrate, the proportion is minimum at a central portion of each of the cermet electrode layers and the proportion is maximum at a circumferential edge of each of the cermet electrode layers.

Specifically, the ratio of Rh is increased at the central portion of each of the cermet electrode layers of the NOx-decomposing electrode. By doing so, the oxidation reaction and the reduction reaction in the measurement of NOx are suppressed at the circumferential edge of each of the cermet electrode layers, and the expansion and the contraction of each of the cermet electrode layers are suppressed. Therefore, the NOx-decomposing electrode is prevented from exfoliation from the ceramic substrate.

As described above, the ratio of Rh is large at the central portion of the NOx-decomposing electrode as compared with the circumferential edge of the NOx-decomposing electrode. Therefore, the ability to decompose NOx is improved in the measurement of NOx.

In particular, the exfoliation of the NOx-decomposing electrode from the ceramic substrate is hardly caused when the NOx-decomposing electrode includes a first cermet electrode layer and a second cermet electrode layer which is formed outside of the first cermet electrode layer; the ratio between Pt and Rh (Pt:Rh) in the first cermet electrode layer ranges from 25:75 to 0:100 by weight; and the ratio between Pt and Rh (Pt:Rh) in the second cermet electrode layer ranges from 100:0 to 25:75 by weight. Accordingly, the service life of the NOx-decomposing electrode of the present invention is twice or more as long as the service life of the conventional NOx-decomposing electrode.

In the NOx-decomposing electrode of the present invention, it is preferable that a ratio between the alloy of Pt—Rh and the ceramic component ((alloy of Pt—Rh):(ceramic component)) in each of the cermet electrode layers ranges from 50:50 to 70:30 in volume.

According to another aspect of the present invention, there is provided a NOx concentration-measuring apparatus comprising a first oxygen pump means for introducing a measurement gas from outside into a first hollow space provided in the NOx concentration-measuring apparatus so that a partial pressure of oxygen in the measurement gas is adjusted; and a second oxygen pump means for pumping out oxygen from the measurement gas having the partial pressure of oxygen controlled by the first oxygen pump means and controlling the partial pressure of oxygen to be a predetermined value at which a NOx component is reduced or decomposed to pump out oxygen produced when the NOx component in an atmosphere in a second hollow space provided in the NOx concentration-measuring apparatus is reduced or decomposed; wherein a concentration of NOx existing in the measurement gas is determined by detecting a pumping current flowing through the NOx concentration-measuring apparatus in accordance with a pumping action of the second oxygen pump means of the NOx concentration-measuring apparatus; and a NOx-decomposing electrode of the second oxygen pump means for reducing or decomposing the NOx component is formed on a ceramic substrate. In this arrangement, the NOx-decomposing electrode has a multilayered structure comprising a plurality of cermet electrode layers each of which includes an alloy of Pt—Rh and a ceramic component. Further, the respective cermet electrode layers have different ratios between Pt and Rh in the NOx-decomposing electrode.

According to still another aspect of the present invention, there is provided a NOx concentration-measuring apparatus comprising a first oxygen pump means for introducing a measurement gas from outside into a first hollow space provided in the NOx concentration-measuring apparatus so that a partial pressure of oxygen in the measurement gas is adjusted; and a second oxygen pump means for pumping out oxygen from the measurement gas having the partial pressure of oxygen controlled by the first oxygen pump means and controlling the partial pressure of oxygen to be a predetermined value at which a NOx component is reduced or decomposed to pump out oxygen produced when the NOx component in an atmosphere in a second hollow space provided in the NOx concentration-measuring apparatus is reduced or decomposed; wherein a concentration of NOx existing in the measurement gas is determined by detecting a pumping current flowing through the NOx concentration-measuring apparatus in accordance with a pumping action of the second oxygen pump means of the NOx concentration-measuring apparatus; the NOx-decomposing electrode is formed on a ceramic substrate; and among the proportions of Pt in the respective cermet electrode layers, the proportion in the lowermost cermet electrode layer formed directly on the ceramic substrate is maximum and the proportion in the uppermost cermet electrode layer is minimum.

According to still another aspect of the present invention, there is provided a NOx concentration-measuring apparatus comprising a first oxygen pump means for introducing a measurement gas from outside into a first hollow space provided in the NOx concentration-measuring apparatus so that a partial pressure of oxygen in the measurement gas is adjusted; and a second oxygen pump means for pumping out oxygen from the measurement gas having the partial pressure of oxygen controlled by the first oxygen pump means and controlling the partial pressure of oxygen to be a predetermined value at which a NOx component is reduced or decomposed to pump out oxygen produced when the NOx component existing in an atmosphere in a second hollow space provided in the NOx concentration-measuring apparatus is reduced or decomposed; wherein a concentration of NOx existing in the measurement gas is determined by detecting a pumping current flowing through the NOx concentration-measuring apparatus in accordance with a pumping action of the second oxygen pump means of the NOx concentration-measuring apparatus; a NOx-decomposing electrode of the second oxygen pump means for reducing or decomposing the NOx component is formed directly on a ceramic substrate; the NOx-decomposing electrode has a multilayered structure comprising a plurality of cermet electrode layers each of which includes an alloy of Pt—Rh and a ceramic component; and the respective cermet electrode layers are formed on the ceramic substrate. In this arrangement, the respective cermet electrode layers have different ratios between Pt and Rh in the respective cermet electrode layers; and among proportions of Pt in the NOx-decomposing electrode layers, the proportion is minimum in the cermet electrode layer formed at a central portion of the NOx-decomposing electrode and the proportion is maximum in the cermet electrode layer formed at a circumferential edge of the NOx-decomposing electrode.

The above and other objects, features, and advantages of the present invention will become more apparent from the following description when taken in conjunction with the accompanying drawings in which a preferred embodiment of the present invention is shown by way of illustrative example.

BRIEF DESCRIPTION OF THE DRAWINGS

FIG. 3 is a table illustrating the ratio between Pt and Rh in first cermet electrode layers of NOx-decomposing electrodes manufactured in a first exemplary experiment;

FIG. 6 is a table illustrating the ratio between Pt and Rh in fourth cermet electrode layers of NOx-decomposing electrodes manufactured in the second exemplary experiment;

DESCRIPTION OF THE PREFERRED EMBODIMENTS

Preferred embodiments of the NOx concentration-measuring apparatus 10 according to the present invention will be explained with reference to FIGS. 1 to 9.

Figure 1:
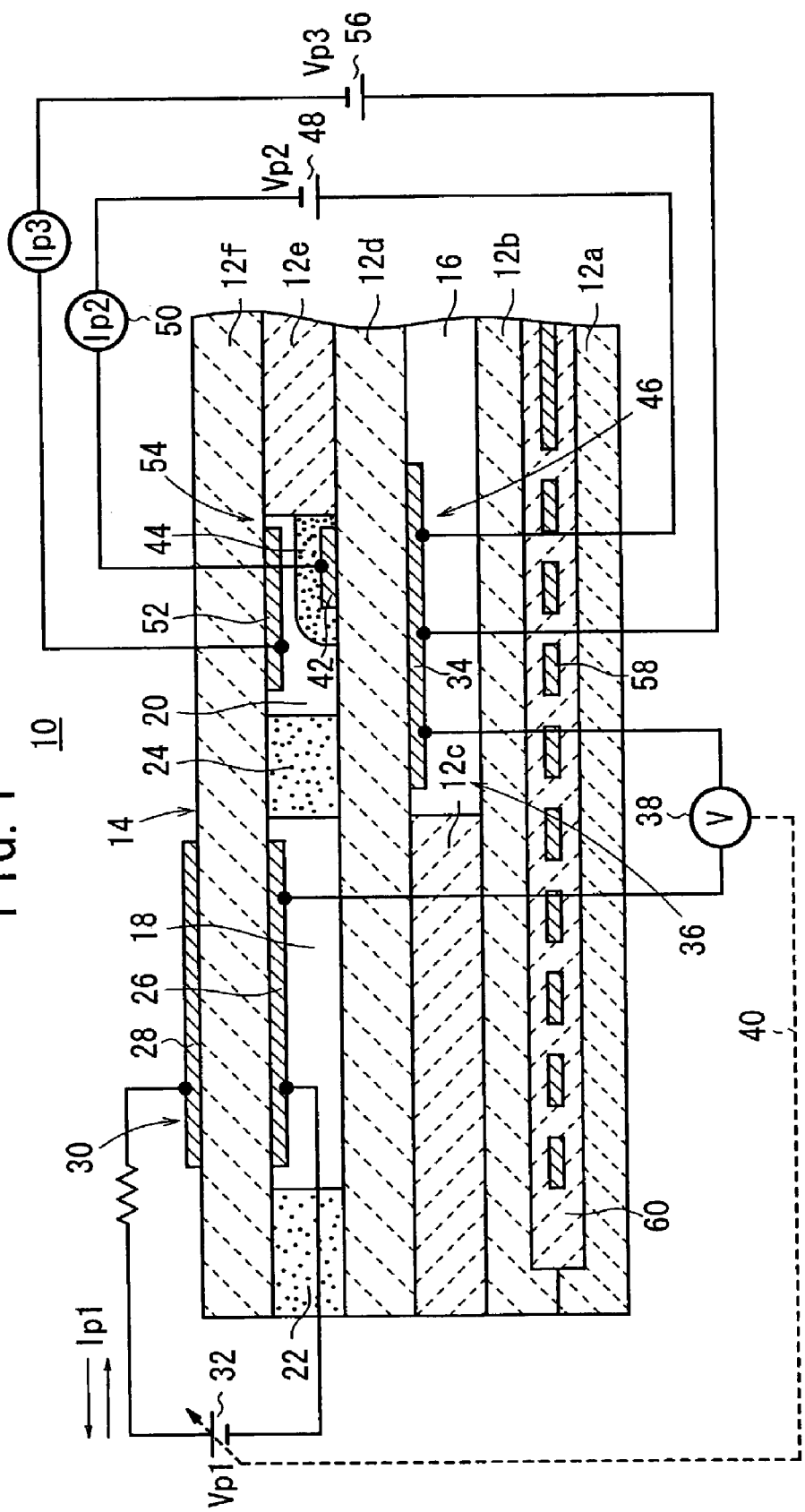
FIG. 1 is a longitudinal sectional view illustrating a NOx concentration-measuring apparatus according to an embodiment of the present invention.

As shown in FIG. 1, a NOx concentration-measuring apparatus 10 has a substrate 14 comprising six laminated solid electrolyte layers 12a to 12f which are ceramics of oxygen ion-conductive solid electrolyte such as $ZrO_2$.

A space (reference gas-introducing space 16), into which a reference gas, for example, the atmospheric air to serve as a reference to measure the oxide is introduced, is formed by the solid electrolyte layers 12b, 12c, 12d in the substrate 14.

The substrate 14 is formed with a first chamber 18 for adjusting the partial pressure of oxygen in the measurement gas, and a second chamber 20 for finely adjusting the partial pressure of oxygen in the measurement gas and measuring the oxide, for example, nitrogen oxides (NOx) in the measurement gas.

In the NOx concentration-measuring apparatus 10, the first chamber 18 of the solid electrolyte layer 12e is communicated with the outside via a first diffusion rate-determining section 22. The first chamber 18 and the second chamber 20 are communicated with each other via a second diffusion rate-determining section 24.

The first and second diffusion rate-determining sections 22, 24 give predetermined diffusion resistances to the measurement gas to be introduced into the first chamber 18 and the second chamber 20, respectively. As shown in FIG. 1, each of the first and second diffusion rate-determining sections 22, 24 is formed as a rectangular slit for introducing the measurement gas. Both of the slits are formed in the solid electrolyte layer 12e.

The slit of the second diffusion rate-determining section 24 may be filled with a porous member including $ZrO_2$ or the like so that the diffusion resistance of the second diffusion rate-determining section 24 is made larger than the diffusion resistance of the first diffusion rate-determining section 22.

A part of the atmosphere in the first chamber 18, to which the predetermined diffusion resistance is applied by the second diffusion rate-determining section 24, is introduced into the second chamber 20.

The second diffusion rate-determining section 24 restricts the amount of oxygen in the measurement gas inflowing into the measuring space (second chamber 20) from the first chamber 18. Accordingly, when a constant DC voltage Vp3 is applied to an auxiliary pumping cell 54 as described later on, a pumping current Ip3, which flows through the auxiliary pumping cell 54, is suppressed.

The NOx concentration-measuring apparatus 10 according to the embodiment of the present invention further comprises a pumping electrode 26 which comprises a porous cermet electrode (for example, a cermet electrode of Pt—$ZrO_2$ containing 1% by weight of Au) and which is provided on the inner wall surface of the first chamber 18. A pumping electrode 28, which faces the pumping electrode 26, is provided on the upper surface of the solid electrolyte layer 12f. An electrochemical pumping cell, i.e., a main pumping cell 30 is constructed by the pumping electrodes 26, 28 and the solid electrolyte layers 12d, 12e, 12f.

When a desired control voltage (pumping voltage) Vp1 is applied to the pumping electrodes 26, 28 of the main pumping cell 30 from a variable DC power source 32 provided outside, a pumping current Ip1 flows through the solid electrolyte layer 12f disposed between the pumping electrodes 26, 28. When the pumping current Ip1 flows, then the oxygen in the atmosphere in the first chamber 18 can be pumped out to the outside, or the oxygen can be pumped into the first chamber 18 from the outside.

A reference electrode 34 is formed at a portion of the lower surface of the solid electrolyte layer 12d for forming the reference gas-introducing space 16. An electrochemical sensor cell, i.e., a cell 36 for controlling oxygen partial pressure-detecting is constructed by the pumping electrode 26, the reference electrode 34, and the solid electrolyte layer 12d.

The cell 36 detects the partial pressure of oxygen in the atmosphere in the first chamber 18 by measuring, with a voltmeter 38, the electromotive force generated between the pumping electrode 26 and the reference electrode 34 based on the difference in oxygen concentration between the atmosphere in the first chamber 18 and the reference gas (atmospheric air) in the reference gas-introducing space 16.

That is, the voltage V1, which is generated between the pumping electrode 26 and the reference electrode 34, is the electromotive force which is generated based on the difference between the partial pressure of oxygen of the reference gas introduced into the reference gas-introducing space 16 and the partial pressure of oxygen of the measurement gas in the first chamber 18. The partial pressure of oxygen in the first chamber 18 can be detected by measuring the voltage V1 by means of the voltmeter 38.

A feedback control system 40 controls the pumping voltage of the variable power source 32 by using the voltage value corresponding to the partial pressure of oxygen detected as described above. That is, the feedback system 40 controls the pumping action of the main pumping cell 30 so that the partial pressure of oxygen in the atmosphere in the first chamber 18 has a predetermined value. Accordingly, it is possible to control the partial pressure of oxygen in the second chamber 20.

Each of the pumping electrodes 26, 28 comprises an inert material having low catalytic activity on NOx, for example, NO contained in the measurement gas introduced into the first chamber 18.

In the NOx concentration-measuring apparatus 10 according to the embodiment of the present invention, a detecting electrode 42, which comprises a substantially rectangular porous cermet electrode, is formed at a portion of the upper surface of the solid electrolyte layer 12d for forming the second chamber 20, the portion being separated from the second diffusion rate-determining section 24. The detecting electrode 42 is coated with an alumina film which constitutes a third diffusion rate-determining section 44. An electrochemical pumping cell, i.e., a measuring pumping cell 46 is constructed by the detecting electrode 42, the reference electrode 34, and the solid electrolyte layer 12d.

When a constant DC voltage Vp2 is applied by a DC power source 48 between the reference electrode 34 and the detecting electrode 42 of the measuring pumping cell 46, the oxygen in the atmosphere in the second chamber 20 can be pumped out to the reference gas-introducing space 16. A pumping current Ip2, which flows in accordance with the pumping action of the measuring pumping cell 46, is detected by an ampere meter 50. Details of the detecting electrode 42 will be described later on.

The DC power source 48 is capable of applying the voltage such that the limiting current is applied to the pumping of oxygen generated during the decomposition of NOx in the measuring pumping cell 46 under the inflow of NOx restricted by the third diffusion rate-determining section 44.

On the other hand, an auxiliary pumping electrode 52, which comprises a porous cermet electrode (for example, a cermet electrode of Pt—$ZrO_2$ containing 1% by weight of Au), is formed at a portion of the lower surface of the solid electrolyte layer 12f for forming the inner wall surface of the second chamber 20. An auxiliary electrochemical pumping cell, i.e., an auxiliary pumping cell 54 is constructed by the auxiliary pumping electrode 52, the solid electrolyte layers 12d, 12e, 12f, and the reference electrode 34.

A material, which does not reduce the NO component in the measurement gas, is used for the auxiliary pumping electrode 52 in the same manner as for the pumping electrode 26 of the main pumping cell 30.

When the constant DC voltage Vp3 is applied by a DC power source 56 provided outside between the reference electrode 34 and the auxiliary pumping electrode 52 of the auxiliary pumping cell 54, the oxygen in the atmosphere in the second chamber 20 can be pumped out to the reference gas-introducing space 16.

Accordingly, the partial pressure of oxygen in the atmosphere in the second chamber 20 is lowered to a value such that the measurement of the amount of the NOx component is not affected thereby when the measurement gas component (NOx) is not reduced or decomposed. In this arrangement, the amount of change of oxygen to be introduced into the second chamber 20 is extremely low as compared with the amount of change in the measurement gas, owing to the main pumping cell 30 disposed for the first chamber 18. Accordingly, the partial pressure of oxygen in the second chamber 20 is controlled to be a constant value.

Therefore, in the NOx concentration-measuring apparatus 10 as described above, the measurement gas, for which the partial pressure of oxygen has been controlled in the second chamber 20, is introduced into the detecting electrode 42.

The NOx concentration-measuring apparatus 10 according to the embodiment of the present invention comprises a plurality of heaters 58 for generating the heat in accordance with the supply of the electric power from the outside, the heaters 58 being embedded under the solid electrolyte layer 12b. The heaters 58 are provided in order to enhance the oxygen ion conductivity in the NOx concentration-measuring apparatus 10. In this arrangement, in order to electrically insulate the heaters 58 from the solid electrolyte layers 12a, 12b, an insulating layer 60 of alumina or the like is charged to the surroundings of the heaters 58.

The heaters 58 are arranged over an entire area ranging from the first chamber 18 to the second chamber 20. Accordingly, each of the first chamber 18 and the second chamber 20 is heated to a predetermined temperature. Each of the main pumping cell 30, the cell 36, and the measuring pumping cell 46 is also heated to a predetermined temperature by the heaters 58.

Figure 2:
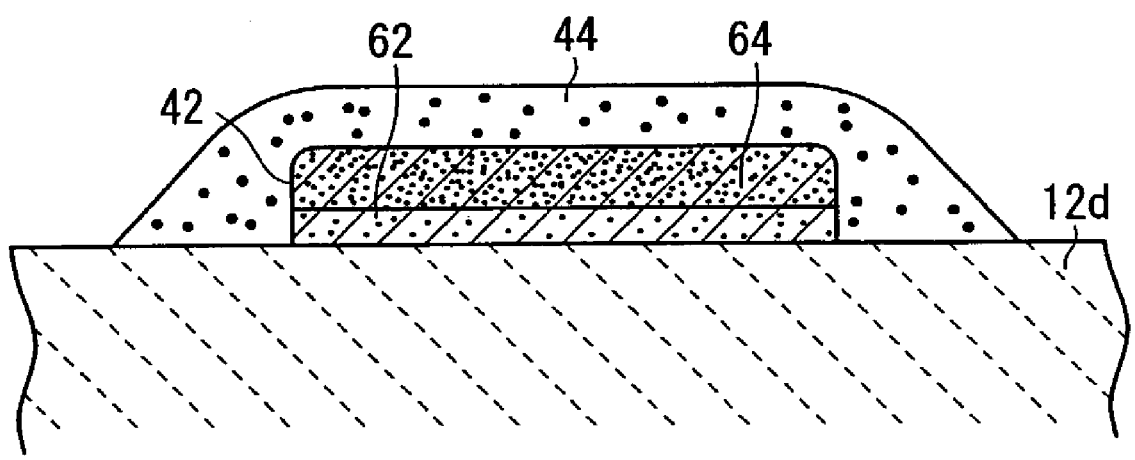
FIG. 2 is a vertical sectional view illustrating a NOx-decomposing electrode according to the embodiment of the present invention.

As shown in FIG. 2, the detecting electrode 42 of the NOx concentration-measuring apparatus 10 according to the embodiment of the present invention has a first cermet electrode layer 62 which is formed directly on the solid electrolyte layer 12d as the substrate, and a second cermet electrode layer 64 which is formed on the first cermet electrode layer 62. Each of the first cermet electrode layer 62 and the second cermet electrode layer 64 is comprises a ceramic component of porous cermet comprising $ZrO_2$ and an alloy of Pt—Rh.

In this arrangement, it is preferable that the ratio between the alloy of Pt—Rh and the ceramic component in each of the first cermet electrode layer 62 and the second cermet electrode layer 64 ((alloy of Pt—Rh):(ceramic component)) ranges from 50:50 to 70:30 in volume.

The first cermet electrode layer 62 and the second cermet electrode layer 64 are formed so that the ratio between Pt and Rh differs. Preferably, in the first cermet electrode layer 62, the ratio between Pt and Rh (Pt:Rh) ranges from 100:0 to 25:75 by weight. On the other hand, in the second cermet electrode layer 64, the ratio between Pt and Rh (Pt:Rh) ranges from 25:75 to 0:100 by weight.

As described above, when the ratios between Pt and Rh are compared with each other for the first and second cermet electrode layers 62, 64, the amount of Pt is large in the first cermet electrode layer 62 as compared with the second cermet electrode layer 64. Therefore, the exfoliation of the detecting electrode 42 from the solid electrolyte layer 12d is suppressed. On the other hand, the amount of Rh is large in the second cermet electrode layer 64 as compared with the first cermet electrode layer 62. Therefore, the ability of the second cermet electrode layer 64 to decompose NOx is improved.

The basic operation of the NOx concentration-measuring apparatus 10 according to the embodiment of the present invention is the same as or equivalent to that of the NOx concentration-measuring apparatus disclosed in Japanese Laid-Open Patent Publication No. 11-183434, any further explanation of which is omitted herein.

Two exemplary experiments will now be described.

In the first exemplary experiment, the change of the exfoliation of the detecting electrode 42 from the solid electrolyte layer 12d (see FIG. 2), i.e., a defect ratio F(t) was tested in relation to the ratio between Pt and Rh in the first cermet electrode layer 62 when the operation and the operation stop of the NOx concentration-measuring apparatus 10 were repeated at a high temperature. The defect ratio F(t) of the NOx concentration-measuring apparatus 10 was obtained with respect to the number of repetition of the operation and the operation stop of the NOx concentration-measuring apparatus 10.

For the first exemplary experiment, as shown in FIG. 3, NOx concentration-measuring apparatuses 10 (Examples 1 to 4) according to the embodiment of the present invention including first cermet electrode layers 62 having different ratios between Pt and Rh, and a NOx concentration-measuring apparatus (Comparative Example 1) including a conventional detecting electrode were manufactured.

Next, an explanation will be made about a method for manufacturing the NOx concentration-measuring apparatuses 10 (Examples 1 to 4) of the first exemplary experiment.

At first, a paste for the first cermet electrode layer 62 is prepared. An alloy, in which the ratio between Rh and Pt satisfies the ratio as shown in FIG. 3 by weight, is used as the alloy of Pt—Rh. The ratio between the alloy of Pt—Rh and $ZrO_2$ (ceramic component) is 60:40 in volume ((alloy of Pt—Rh):(ceramic component)). Further, an organic binder, a plasticizer, and an organic solvent are added to the formulated alloy of Pt—Rh and $ZrO_2$ to prepare the paste for the first cermet electrode layer 62.

Subsequently, a paste for the second cermet electrode layer 64 is prepared. In this case, an alloy, in which the ratio between Pt and Rh (Pt:Rh) is 10:90 by weight, is used as the alloy of Pt—Rh. The ratio between the alloy of Pt—Rh and $ZrO_2$ ((alloy of Pt—Rh):(ceramic component)) is 60:40 in volume. Further, an organic binder, a plasticizer, and an organic solvent are added to the formulated alloy of Pt—Rh and $ZrO_2$ to prepare the paste for the second cermet electrode layer 64.

Subsequently, a green sheet of the solid electrolyte layer 12d is prepared. The green sheet is prepared by mixing a powder of partially stabilized zirconia or fully stabilized zirconia, an organic binder, a plasticizer, and an organic solvent, and by performing, for example, the doctor blade method.

Subsequently, the paste for the first cermet electrode layer 62 is applied to be a thickness from 5 to 15 μm on the green sheet of the solid electrolyte layer 12d by means of the screen printing, and thus a pattern of the first cermet electrode layer 62 is formed.

Subsequently, the paste for the second cermet electrode layer 64 is applied to be a thickness from 15 to 25 μm on the first cermet electrode layer 62 by means of the screen printing, and thus a pattern of the second cermet electrode layer 64 is formed.

Subsequently, an alumina paste is applied to be a thickness of 20 to 50 μm by means of the screen printing so that the entire detecting electrode 42 is covered therewith.

A pattern of the reference electrode 34 is formed on the green sheet of the solid electrolyte layer 12d in addition to the pattern of the detecting electrode 42. Respective patterns of the pumping electrodes 26, 28 and the auxiliary pumping electrode 52 are formed on the green sheet of the solid electrolyte layer 12f. Further, the green sheets as described above are laminated to obtain a laminate.

Subsequently, the laminate is sintered at a high temperature of not less than 1300° C. to obtain the substrate 14. The electrodes including, for example, the detecting electrode 42 as described above are formed on the substrate 14 by means of the sintering.

Subsequently, for example, a housing, a protective cover, and a connector, which are not shown in FIG. 1, are attached to the substrate 14 to obtain each of the NOx concentration-measuring apparatuses 10 (Examples 1 to 4) according to the embodiment of the present invention.

On the other hand, in the case of the NOx concentration-measuring apparatus (Comparative Example 1) including the conventional detecting electrode, an alloy of Pt—Rh, in which Pt:Rh is 10:90 by weight, is used. A paste for the detecting electrode is prepared by performing the formulation ((alloy of Pt—Rh):(ceramic component)) to be 60:40 in volume, and adding an organic binder, a plasticizer, and an organic solvent thereto. The paste for the detecting electrode is applied to be a thickness of 20 to 40 μm on a green sheet of $ZrO_2$ by means of the screen printing to form a pattern of the detecting electrode. The pattern of the detecting electrode is sintered to obtain the detecting electrode. Therefore, the conventional NOx concentration-measuring apparatus (Comparative Example 1) is manufactured in accordance with the same method as that used for the NOx concentration-measuring apparatuses 10 (Examples 1 to 4) according to the embodiment of the present invention except for the method for manufacturing the detecting electrode.

Next, an explanation will be made about a method of measuring the defect ratio F(t) of the NOx concentration-measuring apparatuses 10 (Examples 1 to 4) in the first exemplary experiment.

Each of the NOx concentration-measuring apparatuses 10 (Examples 1 to 4) of the embodiment of the present invention is arranged in an electric furnace. Subsequently, the interior of the electric furnace is heated to be in a high temperature atmosphere so that the temperature of the NOx concentration-measuring apparatus 10 (Examples 1 to 4) is within the range from 700 to 800° C. In this state, the operation and the operation stop of the main pumping cell 30, the measuring pumping cell 46, the auxiliary pumping cell 54, and the heaters 58 of the NOx concentration-measuring apparatus 10 are repeated. The period of time for the operation is 5 minutes, and the period of time for the operation stop is 5 minutes.

When the operation and the operation stop are repeated within 1000 cycles, the NOx sensitivity of the detecting electrode 42, i.e., the pumping current Ip2 is measured by the ampere meter 50 at every 100 cycles. When the repetition is performed by not less than 1000 cycles, the NOx sensitivity of the detecting electrode 42 is measured at every 500 cycles.

When the measured NOx sensitivity is less than 20% of the NOx sensitivity previously measured before performing the experiment, it is assumed that the exfoliation of the detecting electrode 42 from the solid electrolyte layer 12d occurs, and that cracks may appear in the alumina film of the third diffusion rate-determining section 44. Based on the appearance of cracks, it is judged that the NOx concentration-measuring apparatus 10 (Examples 1 to 4) of the first exemplary experiment is deteriorated. The NOx concentration-measuring apparatus 10 is disassembled, and the cross section of the detecting electrode 42 is observed by using an electron microscope to confirm the presence or absence of cracks.

Figure 4:
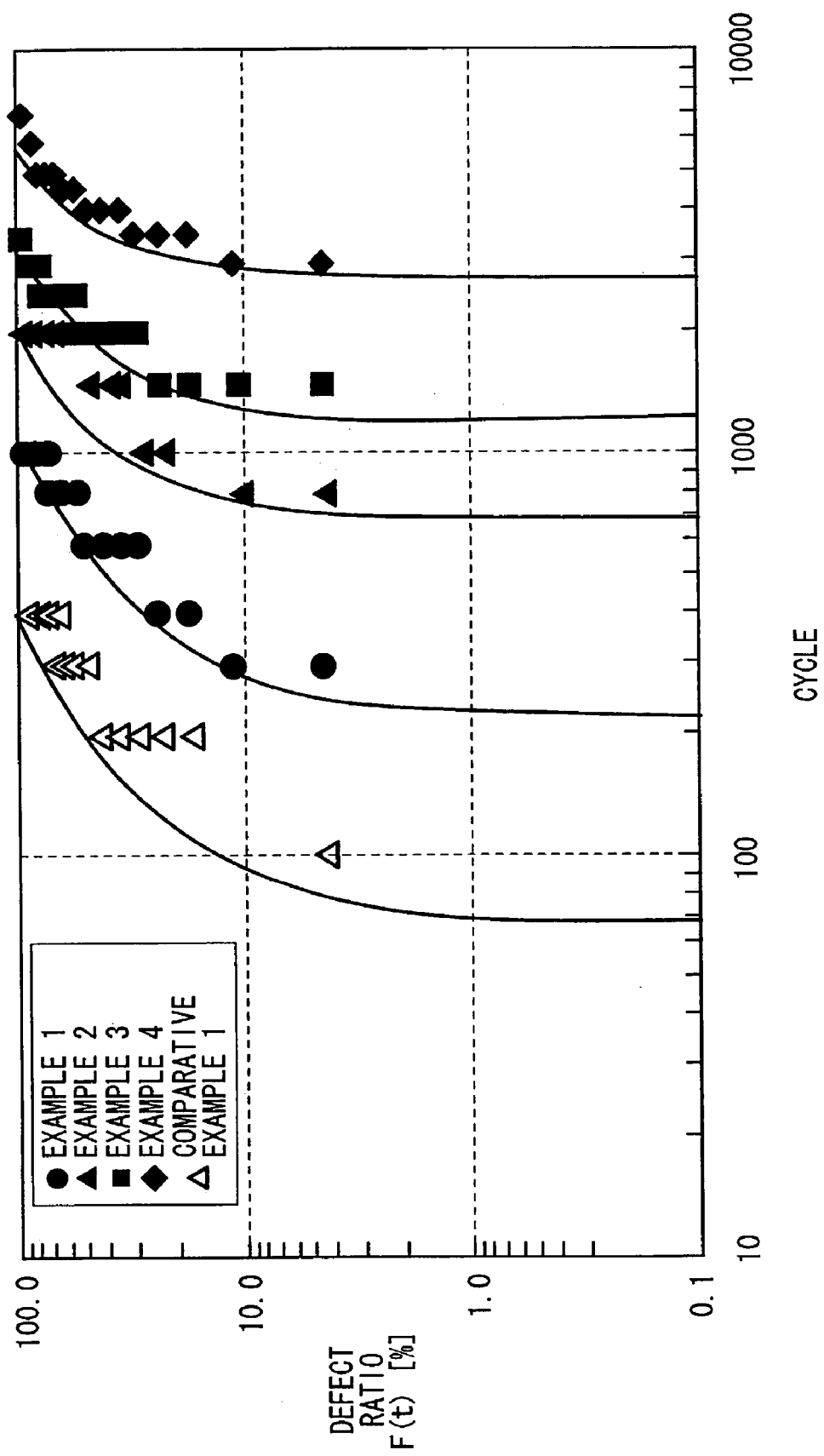
FIG. 4 is a Weibull plot illustrating the defect ratio of the NOx concentration-measuring apparatus manufactured in the first exemplary experiment.

The number of the NOx concentration-measuring apparatuses 10 with cracks is divided by the number of the disassembled NOx concentration-measuring apparatuses 10 is defined as the defect ratio F(t) to prepare a Weibull plot as shown in FIG. 4.

The defect ratio F(t) of the conventional NOx concentration-measuring apparatus (Comparative Example 1) was measured in accordance with the same measuring method as the measuring method of the NOx concentration-measuring apparatuses 10 (Examples 1 to 4) of the first exemplary experiment described above.

FIG. 4 shows the plots of Examples 1 to 4 and Comparative Example 1 which were judged to be deteriorated at the lowest cycles, of the NOx concentration-measuring apparatuses 10 (Examples 1 to 4) of the first exemplary experiment and the conventional NOx concentration-measuring apparatuses (Comparative Example 1) which were judged to be deteriorated.

In Comparative Example 1, F(t) is 0.1% at about 70 cycles. However, in Example 1, F(t) is 0.1% at about 200 cycles. Further, F(t) is 0.1% at about 700 cycles in Example 2, F(t) is 0.1% at about 1200 cycles in Example 3, and F(t) is 0.1% at about 3000 cycles in Example 4. That is, in Examples 1 to 4, the defect ratio F(t) is small and the service life is long as compared with Comparative Example 1.

With reference to FIG. 3, the proportion of Pt, by which the first cermet electrode layer 62 is occupied, is smallest in Example 1, and it is largest in Example 4. When the results shown in FIGS. 3 and 4 are analyzed, the exfoliation of the detecting electrode 42 from the solid electrolyte layer 12d is hardly caused as the proportion of Pt becomes large in the first cermet electrode layer 62. Therefore, the NOx concentration-measuring apparatus 10 of the embodiment of the present invention has the high reliability and the long service life.

Figure 5:
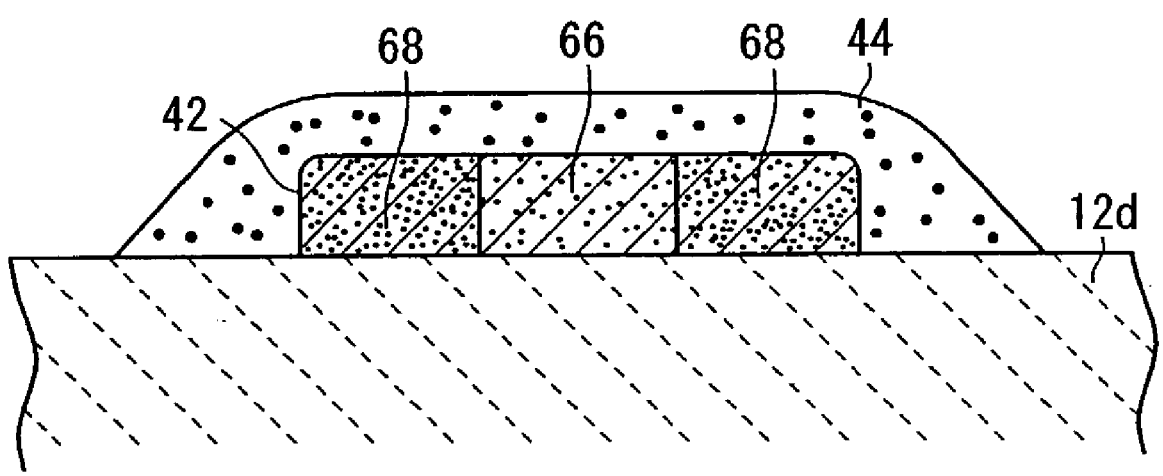
FIG. 5 is a vertical sectional view illustrating a NOx-decomposing electrode manufactured in a second exemplary experiment.

Next, in the second exemplary experiment, as shown in FIG. 5, the change of the defect ratio F(t) of a NOx concentration-measuring apparatus 10 provided with third and fourth cermet electrode layers 66, 68 formed directly on the surface of the solid electrolyte layer 12d was tested. The defect ratio F(t) was obtained with respect to the change of the ratio between Pt and Rh in the alloy of Pt—Rh of the fourth cermet electrode layer 68.

In the second exemplary experiment, as shown in FIG. 6, NOx concentration-measuring apparatuses 10 (Examples 5 to 8) provided with the third and fourth cermet electrode layers 66, 68 having different ratios between Pt and Rh, and a NOx concentration-measuring apparatus (Comparative Example 2) provided with the conventional detecting electrode were manufactured.

At first, a paste for the third cermet electrode layer 66 is prepared. An alloy, in which the ratio between Rh and Pt satisfies the ratio as shown in FIG. 6 by weight, is used as the alloy of Pt—Rh. The ratio between the alloy of Pt—Rh and $ZrO_2$ (ceramic component) is 60:40 in volume ((alloy of Pt—Rh):(ceramic component)). Further, an organic binder, a plasticizer, and an organic solvent are added to the formulated alloy of Pt—Rh and $ZrO_2$ to prepare the paste for the third cermet electrode layer 66.

Subsequently, a paste for the fourth cermet electrode layer 68 is prepared. In this case, an alloy, in which the ratio between Pt and Rh (Pt:Rh) is 10:90 by weight, is used as the alloy of Pt—Rh. The ratio between the alloy of Pt—Rh and $ZrO_2$ ((alloy of Pt—Rh):(ceramic component)) is 60:40 in volume. Further, an organic binder, a plasticizer, and an organic solvent are added to the formulated alloy of Pt—Rh and $ZrO_2$ to prepare the paste for the fourth cermet electrode layer 68.

Subsequently, a green sheet of the solid electrolyte layer 12d is prepared. The method of manufacturing the green sheet is the same as the method used in the first exemplary experiment, any detailed explanation of which is omitted.

Subsequently, the paste for the third cermet electrode layer 66 is applied to be a thickness from 20 to 50 µm on the green sheet of the solid electrolyte layer 12d by means of the screen printing, and thus a pattern of the third cermet electrode layer 66 is formed.

Subsequently, the paste for the fourth cermet electrode layer 68 is applied to be a thickness from 20 to 50 µm on the green sheet of the solid electrolyte layer 12d by means of the screen printing so that the side surface of the third cermet electrode layer 66 is surrounded thereby, and thus a pattern of the fourth cermet electrode layer 68 is formed.

Subsequently, an alumina paste is applied to be a thickness from 20 to 50 µm by means of the screen printing so that the entire detecting electrode 42 is covered therewith. After that, a pattern of the reference electrode 34 is formed on the green sheet of the solid electrolyte layer 12d. Subsequently, respective patterns of the pumping electrodes 26, 28 and the auxiliary pumping electrode 52 are formed on the green sheet of the solid electrolyte layer 12f. Further, the green sheets as described above are laminated to obtain a laminate. Finally, the laminate is sintered at a high temperature of not less than 1300° C. to obtain the substrate 14. The steps of manufacturing the NOx concentration-measuring apparatus 10, which are executed after applying the alumina paste, are the same as the manufacturing steps used in the first exemplary experiment, any detailed explanation of which is omitted herein.

On the other hand, in the case of the NOx concentration-measuring apparatus (Comparative Example 2) including the conventional detecting electrode, an alloy, in which Pt:Rh is 10:90 by weight, is used. A paste for the detecting electrode is prepared by performing the formulation ((alloy of Pt—Rh):(ceramic component)) to be 60:40 in volume, and adding an organic binder, a plasticizer, and an organic solvent thereto. The paste for the detecting electrode is applied to be a thickness from 20 to 50 µm on a green sheet of $ZrO_2$ by means of the screen printing to form a pattern of the detecting electrode. The pattern of the detecting electrode is sintered to obtain the detecting-electrode. Therefore, the conventional NOx concentration-measuring apparatus (Comparative Example 2) is manufactured in accordance with the same method as that used for the NOx concentration-measuring apparatuses 10 (Examples 5 to 8) according to the second exemplary experiment except for the method for manufacturing the detecting electrode., The method of measuring the defect ratio F(t) for the NOx concentration-measuring apparatuses 10 (Examples 5 to 8) of the second exemplary experiment and the conventional NOx concentration-measuring apparatus (Comparative Example 2) is the same as the measuring method used for the NOx concentration-measuring apparatuses 10 (Examples 1 to 4) in the first exemplary experiment.

Figure 7:
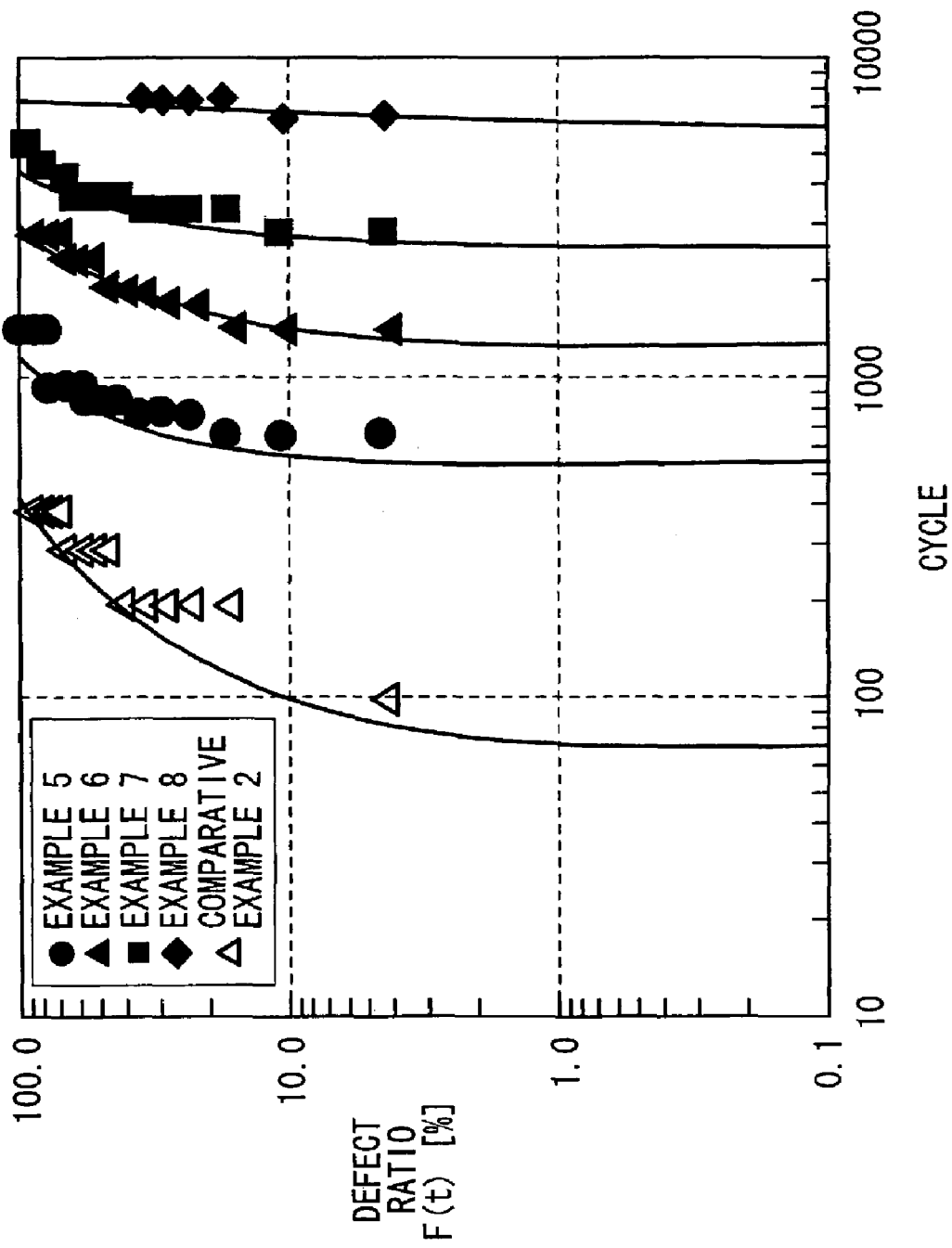
FIG. 7 is a Weibull plot illustrating the defect ratio of the NOx concentration-measuring apparatus manufactured in the second exemplary experiment.

FIG. 7 shows the plots of Examples 5 to 8 and Comparative Example 2 which were judged to be deteriorated at the lowest cycles, of the NOx concentration-measuring apparatuses 10 (Examples 5 to 8) of the second exemplary experiment and the conventional NOx concentration-measuring apparatuses (Comparative Example 2) which were judged to be deteriorated.

In Comparative Example 2, F(t) is 0.1% at about 70 cycles. However, in Example 5, F(t) is 0.1% at about 600 cycles. Further, F(t) is 0.1% at about 1200 cycles in Example 6, F(t) is 0.1% at about 3000 cycles in Example 7, and F(t) is 0.1% at about 6000 cycles in Example 8. That is, the defect ratio F(t) is small and the service life is long in Examples 5 to 8 as compared with Comparative Example 2.

In Examples 5 to 8, the proportion of Pt in the fourth cermet electrode layer 68 is higher than the proportion of Pt in Comparative Example 2. Therefore, the exfoliation of the detecting electrode 42 from the solid electrolyte layer 12d is hardly caused in Examples 5 to 8 as compared with Comparative Example 2.

With reference to FIG. 7, the proportion of Pt, by which the fourth cermet electrode layer 68 is occupied, is smallest in Example 5, and it is largest in Example 8. When the results shown in FIGS. 6 and 7 are analyzed, the exfoliation of the detecting electrode 42 from the solid electrolyte layer 12d is hardly caused as the proportion of Pt becomes large in the fourth cermet electrode layer 68.

In the conventional NOx-decomposing electrode, the exfoliation of the cermet electrode layer from the ceramic substrate was caused at the circumferential edge of the cermet electrode layer. The width of the NOx-decomposing electrode is about several hundreds of μm, and the film thickness of the NOx-decomposing electrode is about several tens of μm. Therefore, the width of the NOx-decomposing electrode is extremely larger than the film thickness of the NOx-decomposing electrode.

Therefore, in view of the suppression of the oxidation and reduction reactions, it is desirable to use the change of the ratio between Pt and Rh in the detecting electrode 42 between the central portion and the circumferential edge of the detecting electrode 42, rather than the change of the ratio in the vertical direction of the detecting electrode 42 as illustrated in the second exemplary experiment.

The ratio of Rh is large in the third cermet electrode layer 66 as compared with the fourth cermet electrode layer 68. Therefore, the ability of the detecting electrode 42 to decompose NOx is improved. On the other hand, the ratio of Pt is large in the fourth cermet electrode layer 68 as compared with the third cermet electrode layer 66. Therefore, the exfoliation of the detecting electrode 42 from the solid electrolyte layer 12d is suppressed.

Therefore, the NOx concentration-measuring apparatus 10 of the embodiment of the present invention has the high reliability and the long service life.

The first and second exemplary experiments described above are illustrative of the case in which the cermet electrode layer of the detecting electrode 42 has the two-layered structure. The cermet electrode layer of the detecting electrode 42 is not limited to the two-layered structure as described above. The cermet electrode layer of the detecting electrode 42 may be formed to have a multilayered structure having three or more layers. In this arrangement, the ratio of Rh in the cermet electrode layer as the uppermost layer is maximum in the first exemplary experiment. In the second exemplary experiment, the ratio of Rh at the central portion of the cermet electrode layer is maximum.

Further, the exfoliation of the detecting electrode 42 from the solid electrolyte layer 12d tends to occur from the circumferential edge of the first cermet electrode layer 62.

Accordingly, when the ratio of Pt is larger than that of Rh at the circumferential edge of the first cermet electrode layer 62 shown in FIG. 2, the oxidation and reduction reactions of the first cermet electrode layer 62 are suppressed, and the exfoliation of the detecting electrode 42 from the solid electrolyte layer 12d is avoided.

Figure 8:
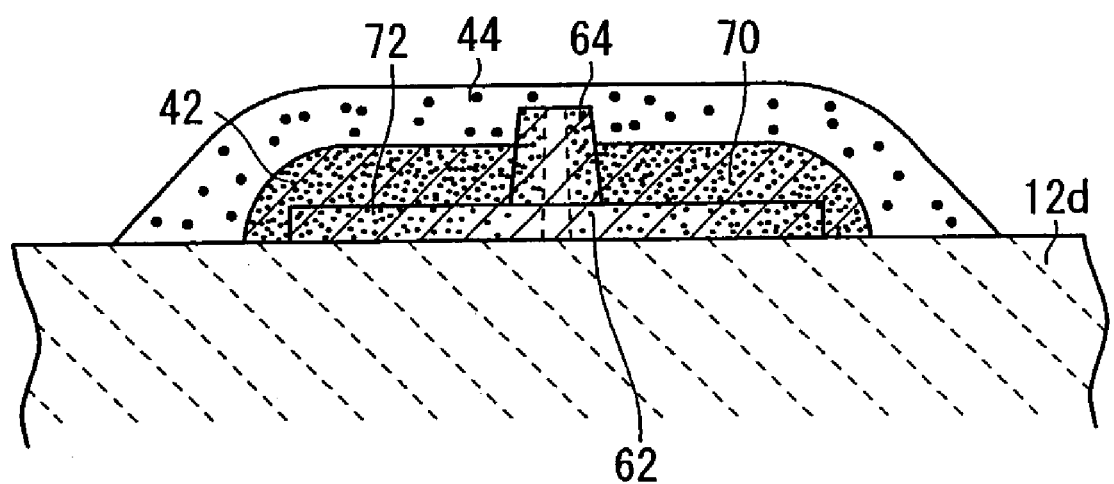
FIG. 8 is a vertical sectional view illustrating a modified embodiment of the NOx-decomposing electrode according to the embodiment of the present invention.

In view of the above, as shown in FIG. 8, a second cermet electrode layer 64, which has a width narrower than that of the first cermet electrode layer 62, is formed on the first cermet electrode layer 62 of a detecting electrode 42, and a fifth cermet electrode layer 70 is formed so that the first cermet electrode layer 62 is covered therewith. In this arrangement, the alloy of the fifth cermet electrode layer 70 comprises Pt.

Further, a diffusion layer 72, in which the proportion of Rh in the alloy of Pt—Rh is changed, is formed between the central portions of the first and second cermet electrode layers 6.2, 64 and the circumferential edges of the first and second cermet electrode layers 62, 64. In this arrangement, the proportion of Rh is maximum at the central portions.

The width of the first cermet electrode layer 62 is about several hundreds of μm, which is sufficiently large as compared with the film thickness of the detecting electrode 42 of several tens of μm. Accordingly, it is possible to form the diffusion layer 72 of Rh.

As described above, in this structure, the proportion of Pt is larger than that of Rh at the circumferential edges of the first and second cermet electrode layers 62, 64, and the alloy is composed of Pt in the fifth cermet electrode layer 70. Therefore, the oxidation reaction and the reduction reaction are suppressed at the circumferential edge of the detecting electrode 42. When the oxidation reaction and the reduction reaction are suppressed, the expansion and the contraction of the detecting electrode 42 are suppressed. Therefore, the exfoliation is avoided between the detecting electrode 42 and the solid electrolyte layer 12d composed of the ceramic material ($ZrO_2$).

The proportion of Rh is larger than that of Pt at the central portions of the first and second cermet electrode layers 62, 64. Therefore, the ability to decompose NOx is improved in the detecting electrode 42.

Figure 9:
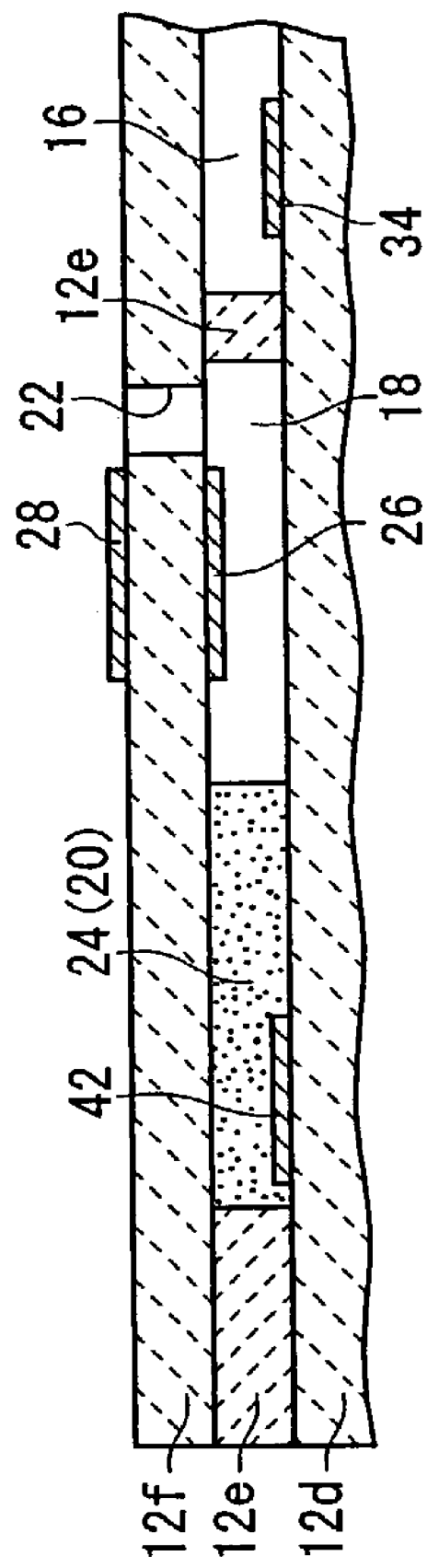
FIG. 9 is a longitudinal sectional view illustrating a modified embodiment of the NOx concentration-measuring apparatus according to the embodiment of the present invention.

As shown in FIG. 9, the second chamber 20 and the second diffusion rate-determining section 24 may be filled with a porous member as a further modified embodiment of the NOx concentration-measuring apparatus 10 according to the embodiment of the present invention.

More specifically, the second chamber 20 and the second diffusion rate-determining section 24 in the NOx concentration-measuring apparatus 10 according to the embodiment of the present invention shown in FIG. 1 may be replaced with the structure shown in FIG. 9. That is, a second diffusion rate-determining section 24, which comprises a porous member such as porous alumina, is formed in a hollow space which is communicated with the first chamber 18. The second diffusion rate-determining section 24 is constituted as the second chamber 20. Accordingly, it is possible to simplify the internal structure of the NOx concentration-measuring apparatus 10.

The diffusion resistance of the second diffusion rate-determining section 24 is larger than the diffusion resistance of the first diffusion rate-determining section 22. Therefore, the atmosphere in the first chamber 18 is not affected by the atmosphere in the second chamber 20.

It is a matter of course that the NOx-decomposing electrode and the NOx concentration-measuring apparatus of the present invention are not limited to the embodiments described above, which may be embodied in other various

What is claimed is:

1. A NOx-decomposing electrode for decomposing or reducing NOx, in which oxygen is produced by decomposing NOx by said electrode, said NOx-decomposing electrode having a multilayered structure comprising a plurality of cermet electrode layers each of which includes an alloy of Pt—Rh and a ceramic component, wherein said respective cermet electrode layers are formed on a ceramic substrate, and said respective cermet electrode layers having different ratios between Pt and Rh in said alloys of Pt—Rh, wherein among proportions of Pt in said respective cermet electrode layers, a proportion of Pt is minimum in said cermet electrode layer formed at a central portion of said NOx-decomposing electrode and a proportion of Pt is maximum in said cermet electrode layer formed at a circumferential edge of said NOx-decomposing electrode.

2. The NOx-decomposing electrode according to claim 1, wherein said NOx-decomposing electrode includes a first cermet electrode layer and a second cermet electrode layer formed outside of said first cermet electrode layer, said ratio between Pt and Rh in said first cermet electrode layer ranges from 25:75 to >0:<100 by weight, and said ratio between Pt and Rh in said second cermet electrode layer ranges from <100:>0 to 25:75 by weight.

3. The NOx-decomposing electrode according to claim 1, wherein a ratio between said alloy of Pt—Rh and said ceramic component in each of said cermet electrode layers ranges from 50:50 to 70:30 in volume.

4. The NOx-decomposing electrode according to claim 3, wherein an average particle size of Rh in each of said cermet electrode layers ranges from 10 to 20 µm.

5. A NOx concentration-measuring apparatus comprising:

a first oxygen pump means for introducing a measurement gas from outside into a first hollow space so that a partial pressure of oxygen in said measurement gas is controlled to be a predetermined value; and a second oxygen pump means for pumping out oxygen from said measurement gas having said partial pressure of oxygen controlled by said first oxygen pump means and controlling said partial pressure of oxygen to be a predetermined value at which a NOx component is reduced or decomposed to pump out oxygen produced when said NOx component existing in an atmosphere in a second hollow space is reduced or decomposed, wherein a concentration of NOx existing in said measurement gas is determined by detecting a pumping current flowing in accordance with a pumping action of said second oxygen pump means of said NOx concentration-measuring apparatus, a NOx-decomposing electrode of said second oxygen pump means for reducing or decomposing said NOx component has a multilayered structure comprising a plurality of cermet electrode layers each of which includes an alloy of Pt—Rh and a ceramic component formed directly on a ceramic substrate, said respective cermet electrode layers are formed along said ceramic substrate, said respective cermet electrode layers have different ratios between Pt and Rh in said alloy of Pt—Rh, and among proportions of Pt in said respective cermet electrode layers, a proportion of Pt is minimum in said cermet electrode layer formed at a central portion of said NOx-decomposing electrode and a proportion of Pt is maximum in said cermet electrode layer formed at a circumferential edge of said NOx-decomposing electrode.

* * * * *